United States Patent
Qiu et al.

(10) Patent No.: US 10,975,025 B2
(45) Date of Patent: Apr. 13, 2021

(54) FLUORINATED OLIGOMERS HAVING PENDANT FUNCTIONAL GROUPS

(71) Applicant: 3M INNOVATIVE PROPERTIES COMPANY, St. Paul, MN (US)

(72) Inventors: Zai-Ming Qiu, Woodbury, MN (US); Miguel A. Guerra, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 616 days.

(21) Appl. No.: 14/356,681

(22) PCT Filed: Dec. 4, 2012

(86) PCT No.: PCT/US2012/067674
§ 371 (c)(1),
(2) Date: May 7, 2014

(87) PCT Pub. No.: WO2013/085864
PCT Pub. Date: Jun. 13, 2013

(65) Prior Publication Data
US 2014/0357822 A1    Dec. 4, 2014

Related U.S. Application Data

(60) Provisional application No. 61/567,173, filed on Dec. 6, 2011.

(51) Int. Cl.
| | | |
|---|---|---|
| C07C 317/18 | (2006.01) | |
| C08F 128/02 | (2006.01) | |
| C07C 309/10 | (2006.01) | |
| C07C 59/135 | (2006.01) | |
| C07C 305/10 | (2006.01) | |
| C08F 214/18 | (2006.01) | |
| C07C 315/02 | (2006.01) | |

(52) U.S. Cl.
CPC .......... *C07C 317/18* (2013.01); *C07C 59/135* (2013.01); *C07C 305/10* (2013.01); *C07C 309/10* (2013.01); *C07C 315/02* (2013.01); *C08F 128/02* (2013.01); *C08F 214/184* (2013.01)

(58) Field of Classification Search
CPC ..... C08F 120/04; C08F 128/02; C08F 130/02
See application file for complete search history.

(56) References Cited

U.S. PATENT DOCUMENTS

| | | | |
|---|---|---|---|
| 2,559,751 A | 7/1951 | Berry | |
| 2,713,593 A | 7/1955 | Brice | |
| 3,083,224 A | 3/1963 | Brace | |
| 3,094,547 A | 6/1963 | Heine | |
| 3,546,186 A * | 12/1970 | Sullivan | ................ C07C 59/315 524/546 |
| 3,577,266 A | 5/1971 | Kirkland | |
| 3,882,153 A * | 5/1975 | Seki | ................ C07C 51/47 554/184 |
| 4,064,067 A | 12/1977 | Lore | |
| 4,349,650 A * | 9/1982 | Krespan | ................ C07C 43/225 204/296 |
| 4,982,009 A | 1/1991 | Hung | |
| 5,608,022 A * | 3/1997 | Nakayama | .......... C08F 214/262 526/212 |
| 6,203,912 B1 | 3/2001 | Watakabe | |
| 6,624,328 B1 | 9/2003 | Guerra | |
| 6,833,418 B2 | 12/2004 | Tan | |
| 7,671,112 B2 | 3/2010 | Hintzer | |

(Continued)

FOREIGN PATENT DOCUMENTS

| | | |
|---|---|---|
| CN | 102024958 | 4/2011 |
| EP | 0 969 045 | 1/2000 |

(Continued)

OTHER PUBLICATIONS

Pedersen, "The Synthesis of Phosphonate Ester Containing Fluorinated Vinyl Ethers", J. Org. Chem., vol. 61, No. 23, pp. 8024-8031 (1996).*

Kotov, "Preparation of perfluorocarbon polymers containing phosphonic acid groups", J. Fluorine Chemistry, vol. 82, No. 1, (Apr. 1, 1997) pp. 13-19.*

Database CA [Online] Chemical Abstracts Service, Columbus, Ohio, US; Kamiya, "Manufacture of aqueous dispersions containing poly(tetrafluoroethylene) columnar microparticles for fiber manufacture", XP 002693165, retrieved from STN Database accession No. 1999:420938 abstract & JP 11 181009 A (Asahi Glass Co., Ltd., Japan) Jul. 6, 1999.

(Continued)

*Primary Examiner* — Nicole M. Buie-Hatcher
(74) *Attorney, Agent, or Firm* — Thomas M. Spielbauer

(57) ABSTRACT

Described herein is an oligomer according to formula I: (I) wherein Y is an anionic group selected from the group consisting of: sulfates, carboxylates, phosphate, phosphonate, and sulfonate, wherein each $X_1$, $X_2$, and $X_3$ are independently selected from F, Cl, H, and $CF_3$; R is a linking group; each $Z_1$ and $Z_2$ is independently selected from F and $CF_3$; m is at least 2; and $R_1$ and $R_2$ are end groups, wherein the oligomer comprises substantially no pendant functional groups, except those selected from the group consisting of: sulfates, carboxylates, phosphate, phosphonate, and sulfonate.

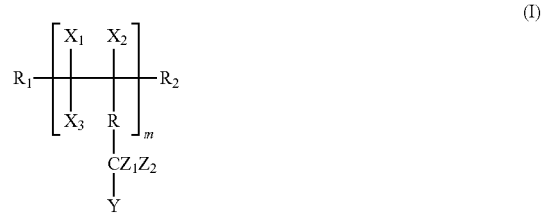

15 Claims, No Drawings

(56) References Cited

U.S. PATENT DOCUMENTS

| | | | |
|---|---|---|---|
| 10,047,175 B2* | 8/2018 | Yamanaka | C08F 2/18 |
| 2001/0029284 A1 | 10/2001 | Nagashima | |
| 2003/0026997 A1* | 2/2003 | Qiu | C04B 41/4884 |
| | | | 428/423.1 |
| 2003/0136938 A1* | 7/2003 | Clark | C08G 18/2885 |
| | | | 252/8.62 |
| 2007/0004848 A1* | 1/2007 | Hintzer | C08F 6/20 |
| | | | 524/544 |
| 2011/0039189 A1 | 2/2011 | Tanuma | |
| 2012/0202946 A1* | 8/2012 | Veneroni | C08F 2/22 |
| | | | 524/805 |
| 2014/0066572 A1* | 3/2014 | Corveleyn | C08G 65/007 |
| | | | 525/50 |

FOREIGN PATENT DOCUMENTS

| | | | |
|---|---|---|---|
| EP | 969045 A1 * | 1/2000 | |
| JP | 60-64990 | 4/1985 | |
| JP | 11-181009 | 7/1999 | |
| JP | H11-209548 | 8/1999 | |
| JP | 2006-513303 | 4/2006 | |
| WO | WO-91/05013 * | 4/1991 | |
| WO | WO 91/05013 | 4/1991 | |
| WO | WO 91/05021 | 4/1991 | |
| WO | WO 1991/005013 | 4/1991 | |
| WO | WO-9952954 A1 * | 10/1999 | C08F 8/44 |
| WO | WO 2004/067588 | 8/2004 | |
| WO | WO 2009/151013 | 12/2009 | |
| WO | WO 2012/082451 | 6/2012 | |
| WO | WO 2012/082454 | 6/2012 | |
| WO | WO 2012/082703 | 6/2012 | |
| WO | WO 2012/082707 | 6/2012 | |
| WO | WO-2012082451 A2 * | 6/2012 | C08F 214/18 |

OTHER PUBLICATIONS

Gramstad, "Perfluoroalkyl Derivatives of Sulphur. Part IV. Perfluoroalkanesulphonic Acids", *J. Chem. Soc.*, 173 (1956) and 2640 (1957).

Kotov, "Preparation of perfluorocarbon polymers containing phosphonic acid groups", *J. Fluorine Chemistry*, vol. 82, No. 1, (Apr. 1, 1997) pp. 13-19 XP 005064240.

Pedersen, "The Synthesis of Phosphonate Ester Containing Fluorinated Vinyl Ethers", *J. Org. Chem.*, vol. 61, No. 23, pp. 8024-8031 (1996) XP002047183.

Emery, et al., "The Development of New Membranes for Proton Exchange Membrane Fuel Cells," ECS Transactions, 2007, 11(1), p. 3-14.

Goto, et al., "Development of Aromatic Polymer Electrolyte Membrane with High Conductivity and Durability for Fuel Cell," Polymer Journal, 2009, 41(2), p. 95-104.

Solovieva, et al., "Polymer Sulfofluoride Films as Carriers for Metalloporphyrin Catalysts," Reactive Polymers, 1991, 16(1), p. 9-17.

Wu, et al., "Mesoscale Modeling of Hydrated Morphologies of 3M Perfluorosulfonic Acid-Based Fuel Cell Electrolytes," Langmuir, 2010, 26(17), p. 14308-14315.

* cited by examiner

FLUORINATED OLIGOMERS HAVING PENDANT FUNCTIONAL GROUPS

CROSS REFERENCE TO RELATED APPLICATIONS

This application is a national stage filing under 35 U.S.C. 371 of PCT/US2012/067674, filed Dec. 4, 2012, which claims priority to U.S. Provisional Application No. 61/567,173, filed Dec. 6, 2011, the disclosure of which is incorporated by reference in its/their entirety herein.

TECHNICAL FIELD

The present disclosure relates to fluorinated oligomers having pendant functional groups and methods of making and using the same. In one embodiment, the fluorinated oligomers of the present disclosure may be used as surfactants.

BACKGROUND

Anionic perfluorinated alkane compounds, such as perfluorooctanic acid and perflurooooctane sulfonic acid and their salts, have been found wide application in industry because of their good performance and unique properties (including inertness). However, the use of some of these anionic perfluorinated alkane compounds, especially those with eight carbons or longer, have been phased out due to environmental concerns.

SUMMARY

There is a desire to identify alternative fluorinated anionic compounds which have at least similar or better performance characteristics (e.g., surface tension) and properties and may be more environmentally acceptable. In one embodiment, the fluorinated anionic compounds may be used in harsh environments such as in strong acidic baths and under electrolysis conditions (e.g., chrome plating or metal treatments).

In one aspect, an anionic oligomer is provided according to formula I:

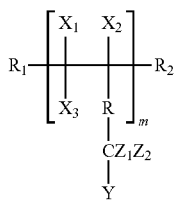

wherein Y is an anionic group selected from sulfates, carboxylates, phosphate, phosphonate, and sulfonate; each $X_1$, $X_2$, and $X_3$ are independently selected from F, Cl, H, and $CF_3$; R is a linking group; each $Z_1$ and $Z_2$ is independently selected from F and $CF_3$; m is at least 2; $R_1$ and $R_2$ are end groups.

In one embodiment, the oligomer comprises substantially no pendant functional groups, except those selected from sulfates, carboxylates, phosphate, phosphonate, and sulfonate.

In another embodiment, the oligomer of Formula 1 further comprises at least one repeating unit of Formula II:

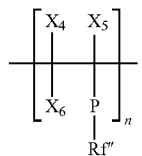

wherein each $X_4$, $X_5$, and $X_6$ are independently selected from F, Cl, H, or $CF_3$; P is a covalent bond or an ether linkage; and Rf' is a perfluorinated alkyl group having 1 to 6 carbons that may comprise at least one catenary heteroatom; and n is at least 1.

In one embodiment, a method for making an anionic fluorinated oligomer is provided comprising i) the oligomerization of fluorinated olefinic monomer with a first functional group, wherein the first functional group can be converted into an anionic group; and ii) converting the first functional group into an anionic group, wherein the anionic group is selected from the group consisting of sulfonate, sulfate, carboxylate, phosphonate or phosphate.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more;
"and/or" is used to indicate one or both stated cases may occur, for example A and/or B includes, (A and B) and (A or B); and
"linking group" refers to a divalent linking group. In one embodiment, the linking group includes at least 1 carbon atom (in some embodiments, at least 2, 4, 8, 10, or even 20 carbon atoms). The linking group can be a linear or branched, cyclic or acyclic structure, that may be saturated or unsaturated, substituted or unsubstituted, and optionally contains one or more heteroatoms selected from the group consisting of sulfur, oxygen, and nitrogen, and/or optionally contains one or more functional groups selected from the group consisting of ester, amide, sulfonamide, carbonyl, carbonate, urethane, urea, and carbamate. In another embodiment, the linking group does not comprise a carbon atom and is a catenary heteroatom such as oxygen, sulfur, or nitrogen.

Also

as used herein, refers to a segment Q (e.g., a monomer) in a compound, such as in an oligomer. In this instance, "p" refers to the number of times segment Q is repeated in the compound and may include either random or block oligomer configurations. For example, in

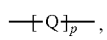, where p is 3, the compound would include block co-oligomer and random co-oligomer configurations, for example, -QQQDDD- as well as -QDQDQD- or -DQQDQD-.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 3, at least 4, at least 6, at least 8, at least 10, at least 25, at least 50, at least 100, etc.).

The present disclosure is directed to anionic oligomers having pendant functional groups selected from sulfates, sulfonates, carboxylates, phosphates, phosphonates, and combinations thereof.

The oligomers of the present disclosure, comprising a repeating segment and two end groups, are shown in Formula I below:

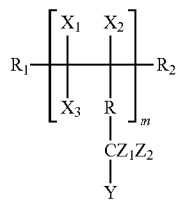

Formula I wherein Y is selected from the group consisting of: sulfates, carboxylates, phosphate, phosphonate, and sulfonate; each $X_1$, $X_2$, and $X_3$ are independently selected from F, Cl, H, and $CF_3$; R is a linking group, which may be saturated or unsaturated, substituted or unsubstituted, and optionally comprises at least one catenary heteroatom; each $Z_1$ and $Z_2$ is independently selected from F and $CF_3$; m is at least 2; and $R_1$ and $R_2$ are end groups.

In one embodiment R may be non-fluorinated, partially fluorinated, or perfluorinated. In some embodiments, the hydrogen atom in R may be replaced with a halogen other than fluorine, such as a chlorine. R may or may not comprise double bonds. R may be substituted or unsubstituted, linear or branched, cyclic or acyclic, and may optionally comprise a functional group (e.g., esters, ethers, ketones, amines, halides, etc.). In one embodiment, R is a catenary heteroatom such as oxygen, sulfur, or nitrogen.

$R_1$ and $R_2$ are end groups generated during oligomerization. Exemplary end groups may be independently selected from hydrogen, iodine, bromine, a linear or branched alkyl, and a linear or branched fluoroalkyl group, optionally containing at least one catenary heteroatom. In some embodiments, the alkyl or fluoroalkyl group has up to 20 carbon atoms. These end groups are typically generated from the initiator or chain transfer agent used to form the oligomer or during a chain transfer reaction. For example, when a nonfluorinated initiator is used, hydrogen atoms may be present as $R_1$ and $R_2$ in Formula I. In one embodiment, $R_1$ and $R_2$ are perfluorinated such as when perfluorinated initiator is used.

In one embodiment of the compound according to Formula I, $X_1$, $X_2$, and $X_3$ are all F and R is a perfluorinated alkylene (in other words, a divalent perfluorinated carbon that may be linear or branched, cyclic or acyclic, may comprise at least one catenary heteroatom, and may comprise 2, 3, 4, 6, 8, 10, 12, 18, or even 20 carbon atoms).

In one embodiment of the compound according to Formula I, R is selected from: $-(CH_2)_a-$, $-(CF_2)_a-$, $-O-(CF_2)_a-$, $-(CF_2)_a-O-(CF_2)_b-$, $-O(CF_2)_a-O-(CF_2)_b-$, and $-(CF_2)_a-[O-(CF_2)_b]_c-$, $-O(CF_2)_a-[O-(CF_2)_b]_c-$, $-[(CF_2)_a-O]_b-[(CF_2)_c-O]_d-$, $-O[(CF_2)_a-O]_b-[(CF_2)_c-O]_d-$, $-O-[CF_2CF(CF_3)O]_a-(CF_2)_b-$, and combinations thereof, wherein a, b, c, and d are independently at least 1, 2, 3, 4, 10, 20, etc.

In some embodiments, the oligomers of the present disclosure are highly fluorinated, meaning that 80%, 90%, 95%, or even 100% of the C—H bonds on the oligomer are replaced by C—F bonds, excluding the pendant anionic functional group (Y) such as the phosphate functional moiety (e.g., $CH_2OP(O)(OM)_2$) and the sulfate functional moiety (e.g., $CH_2OS(O)_2OM$).

In some embodiments, the oligomers of the present disclosure have C—F bonds and no C—H bonds, excluding the pendant anionic functional group (Y). A perfluorinated oligomer of the present disclosure (i.e., Formula I) may comprise partially fluorinated or nonfluorinated end groups, depending on the reaction scheme used to generate the oligomer.

In other embodiments, the oligomers of the present disclosure (i.e., Formula I) are partially fluorinated, meaning that the oligomer (not including the end groups) contains at least one hydrogen atom connected to a carbon in the oligomer and also contains at least one fluorine atom connected to a carbon in the oligomer, excluding the pendant phosphate functional moiety and sulfate functional moiety.

The oligomer of the present disclosure, comprises pendent functional groups selected from the group consisting of: $-SO_3M$, $-CO_2M$, $-SO_2NR'CH_2CO_2M$, $-CH_2OP(O)(OM)_2$, $[-CH_2O]_2P(O)(OM)$, $-CH_2CH_2OP(O)(OM)_2$, $[-CH_2CH_2O]_2P(O)(OM)$, $-CH_2CH_2OSO_3M$, $-P(O)(OM)_2$, $-SO_2NR'CH_2CH_2OP(O)(OM)_2$, $[-SO_2NR'CH_2CH_2O]_2P(O)(OM)$, $-CH_2OSO_3M$, and $-SO_2NR'CH_2CH_2OSO_3M$, and combinations thereof. As used throughout this disclosure M represents a cation.

Exemplary cations useful in the present disclosure include $H^+$, $NH_4^+$, $PH_4^+$, $H_3O^+$, $Na^+$, $Li^+$, $Cs^+$, $Ca^{+2}$, $K^+$, $Mg^{+2}$, $Zn^{+2}$, and $Cu^{+2}$, and/or an organic cation including, but not limited to $N(CH_3)_4^+$, $NH_2(CH_3)_2^+$, $N(CH_2CH_3)_4^+$, $NH(CH_2CH_3)_3^+$, $NH(CH_3)_3^+$, $((CH_3CH_2CH_2CH_2)_4)P^+$, and combinations thereof.

In one embodiment, the oligomer comprises a perfluorinated segment according to Formula Ia:

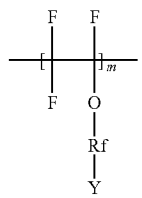

wherein Y is an anionic group, as previously described and m is at least 2. Rf is a perfluorinated divalent linking group which is perfluorinated and may be linear or branched, cyclic or acyclic structure, saturated or unsaturated, substituted or unsubstituted, and optionally contains one or more heteroatoms selected from the group consisting of sulfur, oxygen, and nitrogen.

In one embodiment, the oligomer comprises a partially fluorinated segment according to Formula Ib:

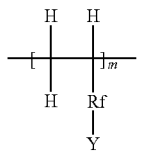

wherein Y is an anionic group as previously described, m is at least 2, and Rf is a perfluorinated divalent linking group as defined in Formula Ia.

Described below are representative oligomers with pendent functional groups and representative processes for preparing them.

Polysulfate Oligomer:

In one embodiment, the anionic group Y in Formula I is a sulfate, for example, —CH$_2$OSO$_3$M, —CH$_2$CH$_2$OSO$_3$M, and —SO$_2$NR'CH$_2$CH$_2$OSO$_3$M, wherein R' is a H, or a C1 to C4 alkyl group and M is a cation.

Exemplary segments comprising a pendent sulfate functional group include: —[CF$_2$CF(OCF$_2$CF$_2$CH$_2$OSO$_3$M)]—, —[CH$_2$CH((CF$_2$)$_4$CH$_2$OSO$_3$M)]—, —[CF$_2$CF(O(CF$_2$)$_4$CH$_2$OSO$_3$M)]—, —[CF$_2$CF(OCF$_2$CF(CF$_3$)CH$_2$OSO$_3$M)]—, —[CF$_2$CF(OCF$_2$CF(CF$_3$)OCF$_2$CF$_2$CH$_2$OSO$_3$M)]—, —[CH$_2$CH((CF$_2$)$_4$CH$_2$OSO$_3$M)]—, —[CF$_2$CF(OCF$_2$CF$_2$SO$_2$N(CH$_3$)CH$_2$CH$_2$OSO$_3$M)]—, —[CH$_2$CH(CF$_2$CF$_2$CH$_2$OSO$_3$M)]—, —[CF$_2$CF(OCF$_2$CF$_2$CF$_2$CF$_2$SO$_2$N(CH$_3$)CH$_2$CH$_2$OSO$_3$M)]—, and —[CH$_2$CH(CF$_2$CF$_2$CH$_2$OSO$_3$M)]—, wherein M is a cation.

Polysulfonate Oligomer

In one embodiment, the anionic group Y in Formula I is a sulfonate, for example, —SO$_3$M, wherein M is a cation.

Exemplary segments comprising a pendent sulfonate functional group include: —[CF$_2$CF(OCF$_2$CF$_2$SO$_3$M)]—, —[CF$_2$CF(O(CF$_2$)$_4$SO$_3$M)]—, —[CF$_2$CF(OCF$_2$CF(CF$_3$)SO$_3$M)]—, —[CF$_2$CF(OCF$_2$CF(CF$_3$)OCF$_2$CF$_2$SO$_3$M)]—, —[CH$_2$CH(CF$_2$CF$_2$SO$_3$M)]—, —[CF$_2$CF(OCF$_2$CF(CF$_3$)OCF$_2$CF$_2$CF$_2$CF$_2$SO$_3$M)]—, —[CH$_2$CH((CF$_2$)$_4$SO$_3$M)]—, —[CH$_2$CH(CF$_2$CF$_2$SO$_3$M)]—, and —[CH$_2$CH((CF$_2$)$_4$SO$_3$M)]—, wherein M is a cation.

Polycarboxylate Oligomer

In one embodiment, the anionic group Y in Formula I comprises a carboxylate, for example —CO$_2$M or —SO$_2$NR'CH$_2$CO$_2$M, wherein R' is H or a C1 to C4 alkyl group and M is a cation.

Exemplary segments comprising a pendent carboxylate functional group include: —[CF$_2$CF(OCF$_2$CF$_2$CO$_2$M)]—, —[CF$_2$CF(O(CF$_2$)$_5$CO$_2$M)]—, —[CF$_2$CF(OCF$_2$CF(CF$_3$)CO$_2$M)]—, —[CF$_2$CF(OCF$_2$CF(CF$_3$)O(CF$_2$)$_n$CO$_2$M)]— where n is greater than 1, —[CH$_2$CH(CF$_2$CF$_2$CO$_2$M)]—, —[CH$_2$CH((CF$_2$)$_4$CO$_2$M)]—, —[CH$_2$CH(CF$_2$CF$_2$CO$_2$M)]—, —[CH$_2$CH((CF$_2$)$_4$CO$_2$M)]—, —[CF$_2$CF(OCF$_2$CF$_2$SO$_2$NR'CH$_2$CO$_2$M)]—, —[CF$_2$CF(O(CF$_2$)$_4$SO$_2$NR'CH$_2$CO$_2$M)]—, —[CF$_2$CF(OCF$_2$CF(CF$_3$)SO$_2$NR'CH$_2$CO$_2$M)]—, —[CF$_2$CF(OCF$_2$CF(CF$_3$)OCF$_2$CF$_2$SO$_2$NR'CH$_2$CO$_2$M)]—, —[CH$_2$CH(CF$_2$CF$_2$SO$_2$NR'CH$_2$CO$_2$M)]—, —[CF$_2$CF(OCF$_2$CF(CF$_3$)OCF$_2$CF$_2$CF$_2$CF$_2$SO$_2$NR'CH$_2$CO$_2$M)]—, —[CH$_2$CH((CF$_2$)$_4$SO$_2$NR'CH$_2$CO$_2$M)]—, —[CH$_2$CH(CF$_2$CF$_2$SO$_2$NR'CH$_2$CO$_2$M)]—, and —[CH$_2$CH((CF$_2$)$_4$SO$_2$NR'CH$_2$CO$_2$M)]—, wherein R' is H or a C1 to C4 alkyl group and M is a cation.

Polyphosphate Oligomer:

In one embodiment, the anionic group Y is a phosphate in Formula I, for example, —CH$_2$OP(O)(OM)$_2$, [—CH$_2$O]$_2$P(O)(OM), —CH$_2$CH$_2$OP(O)(OM)$_2$, [—CH$_2$CH$_2$O]$_2$P(O)(OM), [—SO$_2$NR'CH$_2$CH$_2$O]$_2$P(O)(OM) and —SO$_2$NR'CH$_2$CH$_2$OP(O)(OM)$_2$ wherein R' is a C1 to C4 alkyl group and M is a cation.

Exemplary segments comprising a pendent phosphate functional group include: —[CF$_2$CF(OCF$_2$CF$_2$CH$_2$OP(O)(OM)$_2$)]—, —[CF$_2$CF(O(CF$_2$)$_4$CH$_2$OP(O)(OM)$_2$)]—, —[CF$_2$CF(OCF$_2$CF(CF$_3$)CH$_2$OP(O)(OM)$_2$)]—, —[CF$_2$CF(OCF$_2$CF(CF$_3$)OCF$_2$CF$_2$CH$_2$OP(O)(OM)$_2$)]—, —[CF$_2$CF(OCF$_2$CF$_2$SO$_2$N(CH$_3$)CH$_2$CH$_2$OP(O)(OM)$_2$)]—, —[CF$_2$CF(OCF$_2$CF$_2$CF$_2$CF$_2$SO$_2$N(CH$_3$)CH$_2$CH$_2$OP(O)(OM)$_2$)]—, —[CH$_2$CH(CF$_2$CF$_2$CH$_2$OP(O)(OM)$_2$)]—, —[CH$_2$CH((CF$_2$)$_4$CH$_2$OP(O)(OM)$_2$)]—, —[CH$_2$CH(CF$_2$CF$_2$CH$_2$OP(O)(OM)$_2$)]—, and —[CH$_2$CH((CF$_2$)$_4$CH$_2$OP(O)(OM)$_2$)]—, where M is a cation.

Polyphosphonate Oligomer:

In one embodiment, the anionic group Y in Formula I is a phosphonate, for example —P(O)(OM)$_2$, wherein M is a cation.

Exemplary segments comprising a pendent phosphonate functional group include: —[CF$_2$CF(OCF$_2$CF$_2$P(O)(OM)$_2$)]—, —[CF$_2$CF(O(CF$_2$)$_4$P(O)(OM)$_2$)]—, —[CF$_2$CF(OCF$_2$CF(CF$_3$)P(O)(OM)$_2$)]—, —[CF$_2$CF(OCF$_2$CF(CF$_3$)OCF$_2$CF$_2$P(O)(OM)$_2$)]—, —[CH$_2$CH(CF$_2$CF$_2$P(O)(OM)$_2$)]—, —[CH$_2$CH((CF$_2$)$_4$P(O)(OM)$_2$)]—, —[CH$_2$CH(CF$_2$CF$_2$P(O)(OM)$_2$]—, and —[CH$_2$CH((CF$_2$)$_4$P(O)(OM)$_2$]—, wherein M is a cation.

Method of Making

The pendent functional groups as described above can be formed using techniques known in the art. In one embodiment, the anionic fluorinated oligomer of the present disclosure is made by first oligomerizing a fluorinated olefinic monomer (i.e., a monomer comprising a double bond) having a pendent first functional group and then converting the first functional group into an anionic group, wherein the anionic group is selected from the group consisting of a sulfonate, a sulfate, a carboxylate, a phosphonate, and a phosphate.

The first functional group (i.e., precursor functional group) is a group, which after undergoing a chemical reaction can be converted into a sulfonate, sulfate, carboxylate, phosphonate, or phosphate. In one embodiment, the precursor functional groups may be selected from the following: a hydroxyl group, a carboxylic acid ester group, a phosphate ester group, a sulfonyl fluoride or chloride, a sulfonate ester group, and a sulfinate group, although other techniques and methods as known in the art for obtaining the oligomer of Formula I may be used.

First, fluorinated olefinic monomers comprising a first functional group are oligomerized using techniques known in the art. For example, the oligomerization of fluorinated olefinic monomers may be made as described in U.S. Prov. Appl. Nos. 61/424,146 and 61/424,153 both filed 17 Dec. 2010, herein incorporated by reference in their entirety. Also see U.S. Pat. No. 6,833,418 (Tan et al.), U.S. Pat. No. 6,203,912 (Watakabe et al.) and U.S. Pat. No. 4,982,009 (Hung).

In one embodiment, fluorinated olefinic monomers having the structure according to Formula III or IV may be oligomerized using techniques known in the art:

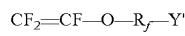  Formula III

  Formula IV

In Formulas III and IV, $R_f$ is linear or branched perfluorinated linking group, which may be saturated or unsaturated, substituted or unsubstituted and optionally comprises at least one catenary heteroatom; and Y' is a precursor (or first) functional group.

In another example, a fluorinated fluorosulfonyl vinyl ether monomer may be oligomerized using techniques known in the art.

In another example, a fluorinated carboxylate easter vinyl ether monomer may be oligomerized using techniques known in the art.

In yet another example, monomers comprising a phosphonate ester monomer may be oligomerized using techniques known in the art. For example, Scot Pedersen and et al. in J. Org. Chem., 61, 8024-8031 (1996) reported the preparation of fluorinated vinyl ether monomer containing phosphonate ester, $CF_2=CF-O-R_f-P(O)(OR'')_2$.

In one embodiment, the monomers may be contacted with a conventional radical initiator in the oligomerization process. Such initiators include, for example, persulfates, peroxides (e.g., organic peroxides, such as diacyl peroxides, peroxyesters, dialkyl peroxides, hyrdoperoxides, etc.), photo irradiation, gamma irradiation, azo compounds, and the like. In some embodiments, more than one initiator may be used. In some embodiments, the initiator is selected from peroxidic compounds. Exemplary peroxidic compounds include: hydrogen peroxide, acyl peroxides (such as, for example, diacetyl peroxide), dipropionyl peroxide, dibutyryl peroxide, dibenzoyl peroxide, benzoyl acetyl peroxide, dilauroyl peroxide, disuccinic peroxide and diglutaric peroxide. In some embodiments, a preferred initiator is selected from perfluorinated peroxide compounds, such as $CF_3C(O)-O-O-C(O)CF_3$, and $CF_3O(CF_2)_2C(O)-O-O-C(O)CF_2CF_2OCF_3$, which can be made from the corresponding perfluorinated carboxylic acid or from the carboxylic acid halide. In addition, water-soluble peracids, such as peracetic acid, and their water-soluble salts (in particular the ammonium, sodium or potassium salts) or their esters, such as, for example, tert-butyl peroxyacetate and tert-butyl peroxypivalate, may be used. The water-soluble salts, in particular the ammonium, potassium and sodium salts of other peracids, such as peroxomono- and peroxodisulfates, perphosphates, perborates and percarbonates may also be employed. Perfluoroacyl peroxides or omega-hydroperfluoroacyl peroxides are furthermore suitable. Azo compounds useful in the present disclosure include azoisobutyronitrile and azo-2-cyanovaleric acid and the like. In some embodiments, certain water-soluble azo compounds are preferred. Conventional active redox systems that generate radicals to an adequate extent at temperatures between 10° C. and 50° C. can also be employed as initiators, above all in the low temperature range. An exemplary redox system includes the combination of water-soluble peroxidic compounds, preferably peroxodisulfates, with hydrogen sulfite or with disulfite or its addition products with formaldehyde, with thiosulfate and with diimine-liberating compounds, such as, for example, with hydrazine or azodicarboxamide may be used. The salts, preferably the alkali metal salts and, in particular, the ammonium salts, of the compounds mentioned are also present in the redox combinations.

In one embodiment, the entire amount of initiator can be added at the beginning of the oligomerization reaction. However, it may be expedient in relatively large batches to add initiator continuously during the course of the oligomerization. Equally, part of the amount of the initiator can alternatively be added at the beginning and the remainder in one or more batches can be added later. The addition of coactivators, i.e. for example, soluble salts of iron and of silver, may be advantageous, in particular when redox systems are used as initiators.

After oligomerization, the oligomers comprising the pendent first functional group may then undergo at least one chemical reaction to convert the first functional group into a second functional group, specifically an anionic functional group, more specifically a sulfonate, a sulfate, a carboxylate, a phosphonate, or a phosphate.

In one embodiment, the oligomer comprises a first functional group of a hydroxyl (o-$CH_2OH$), which can be converted into sulfate and phosphate. At least two different reactions schemes are contemplated. In the first scheme, the oligomer is contacted with concentrated sulfuric acid or $ClSO_3H$, which converts the hydroxyl group into a sulfate group (e.g., —$CH_2OSO_3M$) after neutralization. See for example, U.S. Pat. No. 2,559,751 (Lester et al.), which discloses the preparation of Rf-L-$CH_2OSO_3M$ from Rf-L-$CH_2OH$. In the second scheme, the oligomer is contacted with $P(O)Cl_3$ and limited water, which converts the hydroxyl group into a phosphate group (e.g., —$CH_2OP(=O)(OM)_2$ and/or [—$CH_2O]_2P(=O)(OM)$). See for example, U.S. Pat. No. 3,083,224 (Brace et al.), U.S. Pat. No. 3,094,547 (Heine), and U.S. Pat. No. 4,064,067 (Lore); and JP Pat. No. 60064990 (Kawakami et al.). In the example with $P(O)Cl_3$, $P(O)(OH)_2Cl$ and $P(O)(OH)Cl_2$ may be first formed during the initial reaction with limited water. $P(O)(OH)Cl_2$ may react with the second hydroxyl group on the same oligomer or on a different oligomer to generate, for example, [—$CH_2O]_2P(O)(OM)$, resulting in a cyclic or dimerized molecule In one embodiment, a polyol oligomer may be obtained, such as by reduction of a polycarboxylate. In another embodiment, the polyol oligomer may be obtained by derivatization from a polysulfonyl fluoride or a polycarboxylate ester by reacting with for example, an omega-hydroxylamine.

In another embodiment, the oligomer comprises a first functional group of a carboxylic acid ester. In one reaction scheme the ester is saponified (i.e., hydrolyzed with a base) to the carboxylic acid salt group. Such saponification reactions are known in the art and include, for example, using an acid such as sulfuric acid or a base such as sodium hydroxide. In another reaction scheme, the ester group can be reduced to form a hydroxyl group (alcohol group), which may then be reacted using the reaction schemes described previously.

In another embodiment, the oligomer comprises a first functional group of a phosphate ester. This phosphate ester group can be hydrolyzed to form the phosphoric acid salt group (e.g., —$P(=O)(OM)_2$).

In yet another embodiment, the oligomer comprises a first functional group of a sulfonate ester (e.g., —$SO_3R$). The oligomer can be hydrolyzed to form the sulfonate acid salt group (e.g., —$SO_3M$).

In still another embodiment, the oligomer comprises a first functional group of a sulfonyl fluoride (e.g., —$SO_2F$) or chloride (e.g., —$SO_2Cl$). In one reaction scheme, the oligomer is hydrolyzed to form the sulfonate acid salt group (e.g., —$SO_3M$). A procedure for converting a sulfonyl fluoride to sulfonate can be found, for example, in J. Chem. Soc., 173 (1956) and 2640 (1957) by T. Gramstad and R. N. Haszeldine.

In another reaction scheme, the oligomer comprising a first functional group of a sulfonyl fluoride or chloride is reduced by using a reducing agent to form a sulfinate salt (e.g., —SO$_2$M), which can then be oxidized to form the sulfonate acid salt group.

Exemplary reducing agents useful include those known in the art, such as, for example, metal hydrides, such as MeLH$_4$, where Me is an alkaline metal and L is either an aluminum or a boron and MeH$_x$, where Me is either an alkaline metal or an alkaline earth metal, and x is 1 or 2.

Exemplary oxidizing agents useful include those known in the art, such as, for example, oxygen, permanganate, chromate, perchlorate, and peroxides (e.g., R—O—O—R, wherein each R is independently selected from an alkyl group, an alkyl carbonyl group, H, an aryl group, or a substituted aryl group).

In yet another reaction scheme, a precursor oligomer may be reacted with a compound comprising an amine bearing a terminal first functional group or a second functional group. This reaction scheme enables the incorporation of amines into the oligomer.

In one embodiment, the oligomers of the present disclosure comprise a selection of segments comprising pendent sulfates, carboxylates, phosphate, phosphonate, and sulfonate groups. One skilled in the art can make oligomers comprising the selection of pendent functional groups using the processes described above. For example, an oligomer comprising two different first functional groups can be prepared by co-oligomerization two functionalized monomers and then each of the first functional groups can be converted into the anionic functional group.

In one embodiment, the oligomer of the present disclosure may not comprise additional segments other than those comprising the pendent functional groups described above.

In one embodiment, the oligomers of the present disclosure do not comprise a substantial amount of pendent functional groups aside from sulfates, carboxylates, phosphate, phosphonate, and sulfonate. As used herein, a substantial amount means less than 10, 5, 3, 2, 1, 0.5, or even 0.1% by weight of the functional group versus then weight of the oligomer.

In another embodiment, additional monomers may be introduced into the oligomer to adjust the properties or to reduce the cost of the resulting oligomer. For example, additional monomers may be used to adjust the molecular weight or to change the hydrophobic/hydrophilic nature of the resulting product. In one embodiment, the additional monomers are introduced into the oligomer during oligomerization of the monomers.

In some embodiments, the oligomer of the present disclosure may further comprise a segment according to Formula V:

(V)

wherein Q is derived from a monomer and p is at least 1, 2, 3, 4, 5, 10, 20, etc. Generally, the amount of additional monomer is selected such that the ratio of the additional monomer to the pendent anionic segments described herein is no more than 50, 40, 30 or even 20% mol versus the total.

The additional monomer may be selected from a non-fluorinated olefin, a partially fluorinated olefin, and a perfluorinated olefin.

In one embodiment, the additional monomer is a compound selected from the following formula: CX$_7$X$_8$=CX$_9$ (R$^1$), wherein each of X$_7$, X$_8$, X$_9$ is independently selected from H or F; and R$^1$ is selected from I, Br, and R$_f$—U wherein U=I or Br, and R$_f$ is a perfluorinated or partially perfluorinated alkylene group optionally containing O atoms.

In another embodiment, the additional monomer may be selected from non-fluorinated bromo- or iodo-olefins.

Exemplary additional monomers include, ethylene, tetrafluoroethylene, propylene, hexafluoropropylene, vinyl chloride, vinyl fluoride, vinyl iodide, allyl iodide, a fluoroalkyl substituted ethylene, vinylidene fluoride, fluorinated alkyl vinyl ethers, fluorinated alkoxy vinyl ethers, bromotrifluoroethylene, chlorotrifluoroethylene, and combinations thereof.

Additional exemplary monomers include: CF$_3$CH=CH$_2$, C$_4$F$_9$CH=CH$_2$, CF$_3$OCF=CF$_2$, C$_3$F$_7$OCF=CF$_2$, CF$_2$=CFOCF$_2$CF$_2$CF$_2$OCF$_3$, CF$_2$=CF(CF$_2$)$_2$CF$_2$Br, CHBr=CF$_2$, CF$_2$=CFO(CF$_2$)$_5$CH$_2$OH, CF$_2$=CFO(CF$_2$)$_2$Br, CH$_2$=CHCF$_2$CF$_2$—CH$_2$OH, CH$_2$=CHBr, CF$_2$=CHBr, CH$_2$=CHCH$_2$Br, CF$_2$=CFCF$_2$Br, CH$_2$=CHCF$_2$CF$_2$Br, CF$_2$=CFOCF$_2$CF$_2$Br, CF$_2$=CFCl, CF$_2$=CFCF$_2$Cl, and combinations thereof.

In one embodiment, the oligomer of the present disclosure may comprise even more additional (e.g., second, third, fourth, fifth, etc.) monomer segments selected from a non-fluorinated olefin, a partially fluorinated olefin, a perfluorinated olefin, and combinations thereof.

The resulting oligomer of the present disclosure may be isolated and optionally purified by known methods. In one embodiment, the crude product is isolated from the aqueous reaction mixture by phase separation. In another embodiment, the crude solid is isolated by extracting with a solvent, such as halogenated solvent to remove insoluble inorganic impurity followed by the stripping out of solvent. Useful halogenated solvent are, such as, CH$_2$Cl$_2$, CHCl$_3$, CCl$_4$, ClCH$_2$CH$_2$Cl, C$_4$F$_9$OCH$_3$ and C$_4$F$_9$OCH$_2$CH$_3$.

In some embodiments further purification of the crude product is sometimes not necessary. The elimination of the purification step may reduce processing time and cost. If desired, the reaction mixture or crude product may be purified, for example, by repeated water washing and phase separation.

In one embodiment, resulting oligomers prepared according to the present disclosure may comprise a majority of segments corresponding to formula I, wherein a majority means at least 50, 60, 70 or even 80% by weight of the final product comprises segments corresponding to those in Formula I.

In one embodiment, the resulting oligomers prepared according to the present disclosure have a number average molecular weight of no more than 20,000 grams/mole, 15,000 grams/mole, 10,000 grams/mole, 5,000 grams/mole, 2,000 grams/mole, 1000 grams/mol, or even 500 grams/mole.

The oligomer of the present disclosure may be used to modify the surface energy of a solution. For example, it may be useful as a surfactant, an emulsifier, a leveling agent, or a wetting agent. In one embodiment, the fluorinated anionic compounds may be used for harsh environments such as acidic baths (e.g., chrome plating or metal treatments). The perfluorinated anionic compounds may be especially useful in such environments.

In one embodiment the oligomers of the present disclosure may be used as surfactants. In one embodiment, the oligomers of the present disclosure have a critical micelle concentration of no more than 25, or even 20 dyne/cm.

In one embodiment, the oligomers of the present disclosure have a surface tension of no more than 60, 50, 40, 30, 25, or even 20 dyne/cm at 1000 ppm.

A non-limiting list of exemplary embodiments and combinations of exemplary embodiments of the present disclosure are disclosed below.

Embodiment 1. A composition comprising an oligomer of Formula I:

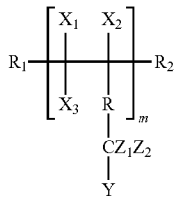

wherein Y is an anionic group selected from the group consisting of: sulfates, carboxylates, phosphate, phosphonate, and sulfonate, wherein each $X_1$, $X_2$, and $X_3$ are independently selected from F, Cl, H, and $CF_3$; R is a linking group; each $Z_1$ and $Z_2$ is independently selected from F and $CF_3$; m is at least 2; and $R_1$ and $R_2$ are end groups, wherein the oligomer comprises substantially no pendant functional groups, except those selected from the group consisting of: sulfates, carboxylates, phosphate, phosphonate, and sulfonate.

Embodiment 2. The composition of embodiment 1, wherein the oligomer comprises a segment according to Formula Ia:

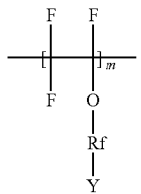

wherein Y is an anionic group selected from the group consisting of: sulfates, carboxylates, phosphate, phosphonate, and sulfonate; Rf is perfluorinated divalent linking group; and m is at least 2.

Embodiment 3. The composition of any one of the previous embodiments, wherein the oligomer comprises a segment according to Formula Ib:

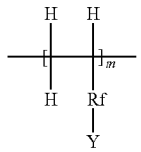

wherein Y is an anionic group selected from the group consisting of: sulfates, carboxylates, phosphate, phosphonate, and sulfonate; Rf is perfluorinated divalent linking group; and m is at least 2.

Embodiment 4. The composition of any one of the previous embodiments, wherein the anionic group is selected from —$SO_3M$, —$CO_2M$-$SO_2NR'CH_2CO_2M$, —$CH_2OP(O)(OM)_2$, —$CH_2CH_2OP(O)(OM)_2$, —$CH_2CH_2OSO_3M$, —$P(O)(OM)_2$, —$SO_2NR'CH_2CH_2OP(O)(OM)_2$, —$CH_2OSO_3M$, and —$SO_2NR'CH_2CH_2OSO_3M$, where M is a cation and R' is a H or a C1 to C4 alkyl group.

Embodiment 5. The composition of any one of the previous embodiments, further comprises at least one repeating unit of Formula II:

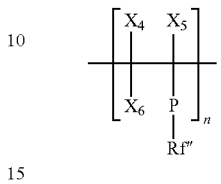

wherein each $X_4$, $X_5$, and $X_6$ are independently selected from F, Cl, H, or $CF_3$; P is a covalent bond or an ether linkage; and Rf' is a perfluorinated alkyl group having 1 to 6 carbons that may comprise a catenary heteroatom; and n is at least 1.

Embodiment 6. The composition of any one of the previous embodiments, wherein M is selected from the group consisting of $K^+$, $Na^+$, $Li^+$, $NH_4^+$, and combinations thereof.

Embodiment 7. The composition of any one of the previous embodiments, wherein the $R_1$ and $R_2$ are perfluorinated.

Embodiment 8. The composition of any one of the previous embodiments, wherein R is —$(CH_2)_a$—, —$(CF_2)_a$—, —O—$(CF_2)_a$—, —O$(CF_2)_a$—, —$(CF_2)_a$—O—$(CF_2)_b$—, —O$(CF_2)_a$—O—$(CF_2)_b$—, —$(CF_2CF(CF_3)O)_a$—, —O$(CF_2CF(CF_3)O)_a$—, —O$(CF_2CF(CF_3)O)_a$—$(CF_2)_b$—, —$(CF_2)_a$—[O—$(CF_2)_b]_c$—, —[$(CF_2)_a$—O$]_b$—[$(CF_2)_c$—O$]_d$—, —[$(CF_2)_a$—O—$]_b$—[$(CF_2CF(CF_3O)_c$—$]_d$—, —O—[$CF_2CF(CF_3)O]_a$—$(CF_2)_b$—, and combinations thereof, wherein a, b, c, and d are independently at least 1.

Embodiment 9. The composition according to any one of the previous embodiments, wherein the $X_1$, $X_2$, and $X_3$ are all F, and —R—$CZ_1Z_2$—Y is —O—$Rf^3$—Y wherein $Rf^3$ is a perfluorinated alkylene.

Embodiment 10. The composition of any one of embodiments 1 or 2, wherein R is a catenary heteratom.

Embodiment 11. The composition according to any one of the previous embodiments, further comprising:

wherein Q is derived from a monomer and p is at least 1.

Embodiment 12. The composition according to embodiment 11, wherein the monomer is selected from a non-fluorinated olefin, a partially fluorinated olefin, a perfluorinated olefin, and combinations thereof.

Embodiment 13. The composition according to any one of embodiments 11-12, wherein the monomer is selected from the following formula: $CX_7X_8$=$CX_9(R^1)$, wherein each of $X_7$, $X_8$, $X_9$ is independently selected from H or F; and $R^1$ is selected from I, Br, and $R_f$—U wherein U=I or Br, and $R_f$ is a perfluorinated or partially fluorinated alkylene group optionally containing O atoms.

Embodiment 14. The composition according to any one of embodiments 11-12 wherein the monomer is selected from: ethylene, tetrafluoroethylene, propylene, hexafluoropropylene, vinyl chloride, vinyl fluoride, a fluoroalkyl substituted ethylene, vinylidene fluoride, allyl iodide, fluorinated alkyl vinyl ethers, fluorinated alkoxy vinyl ethers, bromotrifluoroethylene, chlorotrifluoroethylene, $CF_3CH=CH_2$, $C_4F_9CH=CH_2$, $CF_3OCF=CF_2$, $C_3F_7OCF=CF_2$, and $CF_2=CFOCF_2CF_2CF_2OCF_3$.

Embodiment 15. The composition according to any one of embodiments 1-2, 5-7, and 11-14, wherein the oligomer comprises —[$CF_2$—$CF(OC_4F_8SO_3M)$]$_m$—[$CF_2$—$CF(OC_3F_7)$]—, where M is a cation, m is at least 2 and n is at least 1.

Embodiment 16. A method of using the composition according to anyone of the previous embodiments as a surfactant, dispersant, leveling agent, emulsifier, or wetting agent.

Embodiment 17. A method for making an anionic fluorinated oligomer comprising i) the oligomerization of fluorinated olefinic monomer with a first functional group, wherein the first functional group can be converted into an anionic group; and ii) converting the first functional group into an anionic group, wherein the anionic group is selected from the group consisting of: sulfonate, sulfate, carboxylate, phosphonate, and phosphate.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: bp=boiling point, g=gram; FTIR=Fourier Transform infrared spectroscopy; hr=hour; kPa=kilopascal; mol=mole; ml=milliliter, mm Hg=millimeters of mercury; meq=milliequivalent; N=normal; NMR=nuclear magnetic reasonance; MW=molecular weight; and ppm=parts per million.

Materials/Nomenclature

Example 1: Preparation of a Polysulfonate from Hydrolysis of Poly(Sulfonyl Fluoride)

Preparation of o-MV4S Oligomer: 220 g of MV4S monomer was oligomerized in a 500 mL flask with 20 g "LUPEROX TAEC" peroxide at 110° C. for 4 hrs under nitrogen. An additional 7.01 g "LUPEROX TAEC" was added at 110° C. and reacted for an additional 15 hrs. Distillation was carried out for 2 hrs at 110° C. under full vacuum (<0.5 kPa (4 mm Hg)) to remove unreacted MV4S monomer and low boiling point oligomers to yield 117.1 g o-MV4S oligomer (isolated yield 53%). From $^{19}$F NMR (fluorine-19 nuclear magnetic resonance), no $CF_2=CF$—O— was observed in the o-MV4S oligomer as compared to that of the starting material MV4S. Liquid Chromatography-Mass Spectroscopy (LC-MS) analysis results are summarized in Table 1. Relative areas of the LC-MS indicated the general structure $R^1$—($CF_2$—$CF(OCF_2CF_2CF_2CF_2SO_2F))_n$—$R^2$ where n equals 2-6 and $R^1$ and $R^2$ were either H, $C_2H_5$ or $C_7H_{15}$. The average unit of oligomer had 3.2 units.

TABLE 1

LC-MS for $R^1$—($CF_2$—$CF(OCF_2CF_2CF_2CF_2SO_2F))$n-$R^2$

| | Total % in oligomer | $R^1/R^2$ H/$C_7H_{15}$ | MW | $R^1/R^2$ H/$C_2H_5$ | MW |
|---|---|---|---|---|---|
| n = 2 | 18.00% | 5.40% | 860 | 12.60% | 790 |
| n = 3 | 54.50% | 11.10% | 1240 | 43.40% | 1170 |
| n = 4 | 15.40% | 6.30% | 1620 | 9.10% | 1550 |
| n = 5 | 11.80% | 1.90% | 2000 | 9.90% | 1930 |
| n = 6 | 0.20% | 0.20% | 2380 | * | 2310 |

* Below detection limit

Preparation of a polysulfonate from poly(sulfonyl fluoride): 7.5 g of o-MV4S oligomer was dissolved in 5 g $CH_3OCH_2CH_2OCH_3$, and 2 g distilled water. The solution was treated with 4.5% KOH aqueous solution at room temperature with a magnetic stirring until the pH>8. After reaction for 2 hours, the homogeneous solution showed no —$CF_2SO_2F$ signal at +42 ppm from $^{19}$F NMR analysis,

| Material/Nomenclature | Description and/or Source |
|---|---|
| MV4S | $CF_2=CF$—O—$C_4F_8$—$SO_2F$, made as described in the Example (section A to C) of U.S. Pat. No. 6,624,328 (Guerra) |
| o-MV4S | R—[$CF_2CF(OC_4F_8SO_2F)$]n-R where n = 2-6 and R is H, $C_2H_5$, $CF_3OCF_2CF_2$, and/or $C_7H_{15}$ |
| LUPEROX TAEC | t-amyl peroxy 2-ethylhexyl carbonate commercially available from Arkema, Philadelphia, PA. |
| CTFE-Dimer | Tetrachlorohexafluorobutane, $ClCFClCF_2CFClCF_2Cl$, commercially available from Halocarbon Products Corp., River Edge, NJ |
| o-MV4SO3NH4 | R—[$CF_2CF(OC_4F_8SO_3NH_4)$]n-R where n = 2-5 and R is H, $C_2H_5CF_3OCF_2CF_2$, and/or $C_7H_{15}$ |
| MV5CO2CH3 | $CF_2=CF$—O—$C_5F_{10}$—$CO_2CH_3$, made as described in U.S. Pat. No. 3,546,186 (Karcher et al.) starting with perfluoroadipoyl fluoride available from Exfluor Research Corp., Austin, TX and adding hexafluoropropylene oxide available from DuPont Company Wilington, DE |
| o-MV5CO2H | R—[$CF_2CF(OC5F10CO_2H)$]n-R where n = 2-5 and R can be H, $C_2H_5$ and/or $C_7H_{15}$ |
| o-MV5CO2NH4 | R—[$CF_2CF(OC5F10CO_2NH_4)$]n-R where n = 2-5 and R can be H, $C_2H_5$ and/or $C_7H_{15}$ |
| $CF_2=CFO$—$C_3F_7$ | Available from 3M Co., St. Paul, MN |
| $BrCF_2CF_2CH=CH_2$ | Available from SynQuest Lab, Alachua, FL |
| FC-72 FLUORINERT | A perfluorinated liquid, commercially available from 3M Company, St. Paul, MN under the trade designation "3M FLUORINERT ENGINEERED LIQUID FC-72" | indicating complete hydrolysis. The solution then was acidified with 2N $H_2SO_4$ to a pH<2 and then extracted with t-butylmethyl ether (three times, using 50 mL each time). The combined extraction solutions were then stripped of solvent using rotary evaporation and 5.4 g of the desired product was obtained. The product was diluted with water to form a 10% solution. This solution was neutralized with 1N $NH_4OH$ (i.e., $NH_3$—$H_2O$) and was further diluted with water to make a 5% aqueous solution for surface tension testing.

Example 2: Preparation of a Polysulfonate Via Polysulfinate

Reduction of —[$CF_2$—$CF(OCF_2CF_2CF_2CF_2SO_2F)$]$_n$— to —[$CF_2$—$CF(OCF_2CF_2CF_2CF_2SO_2H)$]$_n$—: A dispersion solution of 16.65 g $NaBH_4$ in 300 g dried THF was made. 116 g o-MV4S oligomer as described in the preparation of the o-MV4S oligomer from Example 1 was dissolved in 106 g dried THF and slowly added to the $NaBH_4$ dispersion solution at room temperature under nitrogen in 2 hours. After addition, the reaction temperature was increased to ~50° C., and reacted for an additional hour at this temperature. The reaction solution was analyzed by $^{19}F$ NMR and all —$SO_2F$ signal had disappeared, and the signal of —$CF_2SO_2$ was shifted from an original –111 ppm (—$CF_2SO_2F$) to –117 ppm and desired –128 ppm (—$CF_2SO_2M$) at the ratio of 1 to 1. Upon subsequent hydrolysis of the solution with $H_2SO_4$—$H_2O$ (2N), the signal at –117 ppm disappeared and the signal at –128 ppm increased, indicating the signal at –117 ppm was —$CF_2SO_2$—B, which converted into —$CF_2SO_2$—H during the acidification. The acidified solution was extraction with t-butylmethylether (3×200 mL each time). The combined extraction were washed with water (50 mL), rotary evaporated to remove solvent yielding 181.5 g of isolated wet polysulfinate product (theoretically 111.3 g product) with a purity of 61%.

Oxidation of —[$CF_2$—$CF(OCF_2CF_2CF_2CF_2SO_2H)$]n- to —[$CF_2$—$CF(OCF_2CF_2CF_2CF_2SO_3NH_4)$]n-: 8.2 g of wet polysulfinate product from above, —[$CF_2$—$CF(OCF_2CF_2CF_2CF_2SO_2H)$]$_n$—, was directly treated with excess $H_2O_2$ aqueous solution (30% wt) at room temperature. The reaction was exothermic and the solution temperature increased to about 60° C. The mixture was allowed to cool to room temperature and then continually stirred at room temperature for one hour. $^{19}F$ NMR analysis showed that all of the —$CF_2SO_2H$ (–130.4 ppm) was converted to $CF_2SO_3H$ (–112.5 ppm). This sample was diluted with water to form a 10% solution. This solution was neutralized with 1N $NH_4OH$ to a pH of ~7.5 and was further diluted with water to make a 5% aqueous solution for surface tension testing.

Example 3: Preparation of Polysulfonate Co-Oligomer from MV4S and $CF_2$=$CFO$—$C_3F_7$ (77 to 23 by Mole Ratio)

In a sealed 500 mL Parr pressure reactor, 105 g MV4S and 26 g $C_3F_7OCF$=$CF_2$ were co-oligomerized in the presence of 10 g LUPEROX TAEC at 110° C. for 5 hours. 135 g of solution was isolated from the reactor. The solution was then distilled at 110° C., then at full vacuum pressure (<4 mmHg) for 1 hours. 46.2 g of oligomer was obtained. From $^{19}F$ NMR analysis, no $CF_2$=$CF$—O— signal was observed and the mole ratio of —$OC_4F_8SO_2F$ and —$OC_3F_7$ was 77 to 23. The co-oligomer of MV4S and $C_3F_7OCF$=$CF_2$ was hydrolyzed with KOH as described in Example 1. The sample was diluted with water to form a 10% solution (5 g of oligomer and 45 g of distilled water). This solution was neutralized with 1N $NH_4OH$ to a pH of ~7.5 and was further diluted with water (about 100 g) to make a 5% aqueous solution for surface tension testing.

Example 4: Preparation of Polysulfonate Co-Oligomer from MV4S and $CF_2$=$CFO$—$C_3F_7$ (87 to 13 by Mole Ratio)

Following the same procedure as described in Example 3, 95 g MV4S and 13 g $C_3F_7OCF$=$CF_2$ were co-oligomerized in the presence of 10 g LUPEROX TAEC at 110° C. for 5 hours. 42 g of oligomer was isolated with the mole ratio of —$OC_4F_8SO_2F$ and —$OC_3F_7$ of 87 to 13. Similarly, the oligomer of MV4S and $C_3F_7OCF$=$CF_2$ was hydrolyzed with KOH and 100 g of 5% aqueous solution was prepared for surface tension testing.

Example 5: Preparation of Polysulfonate Co-Oligomer from Debromo-Sulfination Oligomerization of $BrCF_2CF_2CH$=$CH_2$ and $C_4F_9CH$=$CH_2$ with $Na_2S_2O_4$ Preparation of polysulfinate co-oligomer from debromo-sulfination oligomerization of $BrCF_2CF_2CH$=$CH_2$ and $C_4F_9CH$=$CH_2$ with $Na_2S_2O_4$: 138 g deionized water, 100 g $CH_3CN$ and 25 g $NaHCO_3$ were charged into a 600 mL PARR pressure reactor. The solution was bubbled with nitrogen gas for 2 minutes to remove oxygen. 50 g $BrCF_2CF_2CH$=$CH_2$ and 10 g $C_4F_9CH$=$CH_2$ (available from Aldrich) were then added under a nitrogen atmosphere, followed by 58 g $Na_2S_2O_4$. The reactor was sealed and reacted at 60° C. (internal temperature) with stirring for 24 hours. After cooling to 20° C., the remaining pressure was released, and 353 g liquid (2 phases) with some solids was obtained. $^{19}F$ NMR analysis indicated fluorinated products in the upper phase, but not the lower phase. The solution was filtered to remove solids and 115 g of the top clear solution was isolated. Rotary evaporation of the top phase to remove solvent yielded 33 g of a semisolid. The semisolid was acidified with 2N $H_2SO_4$ to a pH of about 1, and then extracted twice with 200 mL t-butylmethyl ether. The solvent from the combined extracts was removed by rotary evaporation and the remaining liquid was dried under full vacuum overnight to yield 31.26 g of a clear liquid. $^{19}F$ NMR analysis indicated a signal corresponding to $CF_3CF_2CF_2CF_2$—, a small amount of $BrCF_2$— and complicated multiple signals between –113 and –134 ppm (chemical shift) indicating the presence of sulfinate group (—$CF_2SO_2Na$). No $CH_2$=$CH$— signal was observed from the isolated product by FT-IR and $^1H$-NMR analyses. GPC (gas phase chromatography) analysis showed a number average molecular weight of 810 g/mol, a weight average molecular weight of 990 g/mol and a polydispersity of 1.2.

Oxidation of polysulfinate co-oligomer: 5 g sulfinate oligomer (made from above debromo-sulfionation oligomerization of $BrCF_2CF_2CH$=$CH_2$ and $C_4F_9CH$=$CH_2$ with $Na_2S_2O_4$) was oxidized with excess 30% $H_2O_2$ to make the sulfonated oligomer. The reaction was monitored by $^{19}F$-NMR which showed a decreased signal at around –128 to –134 ppm, and increased signal around –110 to –120 ppm. A 100 g of 5% solution was made for surface tension testing.

Example 6: Preparation of Polysulfonate Oligomer by Oligomerization of MV4S with $(CF_3OC_2F_4CO_2)_2$ Preparation of $(CF_3OC_2F_4CO_2)_2$: 280 g (1.2 mol) $CF_3OC_2F_4COF$ (made by electrochemical fluorination as described in example 2 of U.S. Pat. No. 2,713,593 to Brice et al) was added to excess methanol cooled to −20° C. in a 1 L 3-neck round bottom flask. This solution was then water washed to isolate 295 g (1.2 mol) $CF_3OC_2F_4CO_2CH_3$ as the fluorochemical lower phase. A charge of 89 g (1.35 mol) KOH in 150 g water was then added to the isolated lower phase to form the $CF_3OC_2F_4CO_2K$ salt. The salt was dried, then acidified with 150 g of concentrated $H_2SO_4$ in 150 g water, and then vacuumed distilled to isolate 314 g (1.3 mol) of $CF_3OC_2F_4CO_2H$.

50 g (0.22 mol) $CF_3OC_2F_4CO_2H$, 4 g dimethylformamide, and 30 g (0.2.5 mol) thionyl chloride were reacted in a 500 mL 3-neck round bottom flask at 72° C. for one hour followed by distillation to give 46 g (0.19 mol) $CF_3OC_2F_4COCl$. To a 250 ml 3-neck round bottom flask was added 4.7 g (0.05 mol) 35% HOOH which was then cooled to 0° C. with stirring, followed by the addition of 4 g (0.1 mol) of NaOH in 90 g water. The reaction was kept at 10° C. and held for 30 min followed by addition at 10° C. of 20 g (0.08 mol) $CF_3OC_2F_4COCl$ in 180 g of "FC-72 FLUORINERT". The solution was stirred at 10° C. for 30 min and the lower phase was removed containing 10 weight % $CF_3OC_2F_4C(O)OOC(O)C_2F_4OCF_3$ in FC-72 FLUORINERT confirmed by $^{19}$F-NMR and FTIR.

Oligomerization of MV-4S with $CF_3OC_2F_4C(O)O—OC(O)C_2F_4OCF_3$: 120 g (0.32 mol) MV4S was added to a 500 ml 3-neck round bottom flask with a stir bar and cooled to 0° C. This was followed by addition of 100 g of 10 weight percent (0.02 mol) $CF_3OC_2F_4C(O)OOC(O)C_2F_4OCF_3$ in FC-72 FLUORINERT with stirring at 10° C. for 2 hrs. The solution was further reacted for 20 hrs at 25° C. The product mixture was fractionated to give 11 g of o-MV4S having a boiling point greater that 150° C. at 8 mm vacuum. $F^{19}$NMR confirmed the desired perfluorinated o-MV4S having $CF_3OCF_2CF_2—$ end groups and the general structure $CF_3OCF_2CF_2—[CF_2CF(OC_4F_8SO_2F)]n-CF_2CF_2OCF_3$ where n was an average of 15. The oligomer had an average molecular weight of 6050 g per mole under this reaction condition and work up.

The high MW (molecular weight) oligomer with $CF_3OCF_2CF_2—$ end group from above was hydrolyzed to make the corresponding $CF_3OCF_2CF_2—[CF_2CF(OC_4F_8SO_3NH_4)]_n—CF_2CF_2OCF_3$ oligomer which showed low solubility in water.

Example 7: Preparation of Polysulfonate Oligomer by Oligomerization of MV4S in CTFE-Dimer Solvent Oligomeric fluoromultisulfinic acid ammonium salt was made by first oligomerization of MV4S fluoromonomer to o-MV4S. 430 g (1.13 mol) MV4S, 100 g CTFE-Dimer and 58 g (0.25 mol) LUPEROX 575 were charged to an evacuated 600 ml SERIES 4520 PARR reactor, commercially available from Parr Instruments, Moline, Ill. The mixture was stirred and heated to 65° C. for 20 hours. A slight pressure rise was measured and vented after the reaction reached 20° C. A product mixture was drained and fractionated to give 134 g of o-MV4S boiling greater than 220° C. and 50 mm that remained in the pot. The higher boiling material was subjected to LCMS and relative areas indicated the general structure $R—[CF_2CF(OC_4F_8SO_2F)]_n—R$ where n=2-5 and R was H, $C_2H_5$ and/or $C_7H_{15}$. The average oligomer was 2.9 units for an average molecular weight of 1200 g/mol. The oligomer was hydrolyzed with caustic, acidified, and treated with ammonium hydroxide and vacuum dried to make o-MV4SO3NH4.

Example 8A and 8B: Preparation of Polycarboxylate Oligomers

Oligomeric fluoromulticarboxylic acid ammonium salt was made by oligomerization of MV5CO2CH3 fluoromonomer to o-MV5CO2CH3. 200 g (0.49 mol) MV5CO2CH3 and 20 g (0.09 mol) LUPEROX 575 were charged to an evacuated 600 ml SERIES 4520 PARR reactor, commercially available from Parr Instruments, Moline, Ill. The mixture was stirred and heated to 65° C. for 20 hours. A slight pressure rise was measured and vented after the reaction reached 20° C. A product mixture was drained and fractionated to give 89 g of o-MV5CO2CH3 after removing the starting material. Two cuts were obtained by vacuum fractionation of cut 1 from 62-200° C./1 mm vacuum of 54 g and the greater than 200° C./1 mm of 35 g cut 2 in the pot. The materials were subjected to LCMS and relative areas indicated the general structure $R—[CF_2CF(OC_5F_{10}CO_2CH_3)]_n—R$ where n=2-5 and R was H, $C_2H_5$ and/or $C_7H_{15}$. The average oligomer was 2.09 units for an average molecular weight of 950 g/mol for cut 1 (Example 8A), and 2.93 units for an average molecular weight of 1290 g/mol for cut 2 (Example 8A). The oligomer was reacted with sodium hydroxide, vacuum stripped to remove methanol, acidified with concentrated sulfuric acid and made into the ammonium salt by titration with ammonium hydroxide and vacuum dried to make o-MV5CO2NH4.

Surface Tension Measurement

The surface tension was tested as follows: various dilutions of each of the above Examples and Comparative Examples were prepared. A Kruss Tensiometer (model K12, from Kruss USA, Matthews, N.C.) was used to take at least five measurements of each dilution. The measurements were continued until the standard deviation of the last five measurements was 0.07 dyne/cm or less. The average of the last five measurements was reported for each concentration point.

Examples 1-5, 7, 8A and 8B from above where diluted in water. The results of the Surface Tension Measurement from Examples 1-5, 7, 8A and 8B are shown in Table 1 below. The concentration used for each sample was within 1 ppm of the value listed in Table 1.

TABLE 1

| Conc. | Surface Tension (dyne/cm) for the Examples | | | | | | | |
|---|---|---|---|---|---|---|---|---|
| (ppm) | 1 | 2 | 3 | 4 | 5 | 7 | 8A | 8B |
| 0 | 74.00 | 74.22 | 74.24 | 73.08 | 73.15 | 73.48 | 72.50 | 72.64 |
| 124 | 49.78 | 56.95 | 72.11 | 39.73 | 45.49 | 73.18 | 38.42 | 51.03 |
| 307 | 34.19 | 45.59 | 49.12 | 25.28 | 32.98 | 44.52 | 32.76 | 42.45 |
| 572 | 30.93 | 36.57 | 37.46 | 21.94 | 29.73 | 33.38 | 29.56 | 37.93 |
| 935 | 29.05 | 29.38 | 31.87 | 20.57 | 26.75 | 27.65 | 28.22 | 36.98 |
| 1403 | 27.97 | 27.43 | 33.59 | 19.99 | 25.62 | 26.65 | 26.65 | 36.08 |
| 1958 | 26.82 | 25.74 | 23.5 | 19.69 | 21.94 | 25.12 | 25.61 | 36.05 |
| 2556 | 26.1 | 25.64 | 21.52 | 19.04 | 21.15 | 23.25 | 21.05 | 33.32 |

Dilutions of Example 6 were done using a 5% isopropyl alcohol aqueous solution. The results of the Surface Tension Measurement from Example 6 are shown in Table 2 below.

TABLE 2

| Conc. ppm | Surface Tension, dyne/cm |
|---|---|
| 0 | 74.07 |
| 41 | 71.71 |
| 102 | 67.23 |
| 190 | 62.39 |
| 311 | 58.73 |
| 466 | 56.07 |
| 651 | 52.22 |

Comparative Example 1 (CE1) was $CF_3OCF_2CF_2CF_2OCFHCF_2CO_2NH_4$ prepared as described in U.S. Pat. No. 7,671,112 (Hintzer et al.).

Comparative Example 2 (CE2) is $C_7F_{17}CO_2NH_4$, also known as ammonium perfluorooctanoic acid.

Comparative Example 3 (CE3) is $C_8F_{17}SO_3K$, also known as perfluorooctane sulfonate potassium salt.

Each comparative example was diluted in water to a given concentration and the surface tension measured. The results of the Surface Tension Measurement are shown in Table 3 below.

TABLE 3

| Conc. (ppm) | Surface Tension (dyne/cm) for the Comparative Examples | | |
|---|---|---|---|
| | CE 1 | CE 2 | CE 3 |
| 936 | 63.12 | NT | NT |
| 1000 | NT | NT | 33 |
| 1210 | NT | 52.28 | NT |

NT = not tested

As shown in the above Tables, the oligomers of the present disclosure, have surface tension values similar to or lower than the comparative examples.

Foreseeable modifications and alterations of this invention will be apparent to those skilled in the art without departing from the scope and spirit of this invention. This invention should not be restricted to the embodiments that are set forth in this application for illustrative purposes. To the extent that there is a conflict or discrepancy between this specification and the disclosure in any document incorporated by reference herein, this specification will control.

What is claimed is:

1. A composition comprising a compound, wherein the compound consists of end groups $R_1$ and $R_2$ and at least m repeating segments of the following structure:

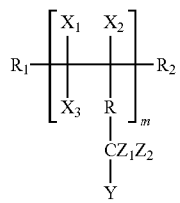

wherein Y is an anionic group selected from the group consisting of: sulfate, carboxylate, phosphate, phosphonate, and sulfonate, wherein each $X_1$, $X_2$, and $X_3$ are independently selected from F, Cl, H, and $CF_3$; R is a linking group; each $Z_1$ and $Z_2$ is independently selected from F and $CF_3$; m is at least 2; wherein the compound comprises substantially no other anionic pendant functional groups, except those selected from the group consisting of: sulfate, carboxylate, phosphate, phosphonate, and sulfonate, wherein the compound has a number average molecular weight of no more than 10,000 grams/mole and an average number of anionic groups of greater than 2.

2. The composition of claim 1, wherein the at least m repeating segments have the following structure:

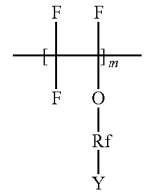

wherein Y is an anionic group selected from the group consisting of: sulfate, carboxylate, phosphate, phosphonate, and sulfonate; Rf is perfluorinated divalent linking group; and m is at least 2.

3. The composition of claim 1, wherein the at least m repeating segments have the following structure:

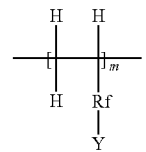

wherein Y is an anionic group selected from the group consisting of: sulfate, carboxylate, phosphate, phosphonate, and sulfonate; Rf is perfluorinated divalent linking group; and m is at least 2.

4. The composition of claim 1, wherein the anionic group is selected from —$SO_3M$, —$CO_2M$, —$SO_2NR'CH_2CO_2M$, —$CH_2OP(O)(OM)_2$, —$CH_2CH_2OP(O)(OM)_2$, —$CH_2CH_2OSO_3M$, —$P(O)(OM)_2$, —$SO_2NR'CH_2CH_2OP(O)(OM)_2$, —$CH_2OSO_3M$, and —$SO_2NR'CH_2CH_2OSO_3M$, where M is a cation and R' is a H or a $C_1$ to $C_4$ alkyl group.

5. The composition of claim 4, wherein M is selected from the group consisting of $K^+$, $Na^+$, $Li^+$, $NH_4^+$, and combinations thereof.

6. The composition of claim 1, wherein R is —$(CH_2)_a$—, —$(CF_2)_a$—, —O—$(CF_2)_a$—, —$O(CF_2)_a$—, —$(CF_2)_a$—O—$(CF_2)_b$—, —$O(CF_2)_a$—O—$(CF_2)_b$—, —$(CF_2CF(CF_3)O)_a$—, —$O(CF_2CF(CF_3)O)_a$—, —$O(CF_2CF(CF_3)O)_a$—$(CF_2)_b$—, —$(CF_2)_a$—[O—$(CF_2)_b$]$_c$—, —[$(CF_2)_a$—O]$_b$—[$(CF_2)_c$—O]$_d$—, —[$(CF_2)_a$—O-]$_b$-[$(CF_2CF(CF_3)O)]_d$—, —O—[$CF_2CF(CF_3)O]_a$—$(CF_2)_b$—, and combinations thereof, wherein a, b, c, and d are independently at least 1.

7. The composition of claim 1, wherein the $X_1$, $X_2$, and $X_3$ are all F, and R—$CZ_1Z_2$—Y is O—Rf³—Y wherein Rf³ is a perfluorinated alkylene.

8. The composition of claim 1, wherein the $R_1$ and $R_2$ are perfluorinated.

9. The composition of claim 1, wherein R is a catenary heteroatom.

10. The composition of claim 1, wherein the compound has a number average molecular weight of no more than 5,000 grams/mole.

11. The composition of claim 1, wherein the compound is a liquid.

12. The composition of claim 1, wherein at least one of $X_1$, $X_2$, and $X_3$ is H.

13. The composition of claim 1, wherein m is an integer from 2-6.

14. The composition of claim 1, wherein the composition comprises no more than 1000 parts per million of the compound.

15. The composition of claim 1, wherein the composition comprises 1000 parts per million of the compound and has a surface tension of no more than 60 dyne/cm.

* * * * *